(12) United States Patent
Dennison

(10) Patent No.: US 7,869,642 B2
(45) Date of Patent: Jan. 11, 2011

(54) WINDOW LEVELING SYSTEM AND METHOD

(75) Inventor: Donald K. Dennison, Waterloo (CA)

(73) Assignee: AGFA Inc., Toronto (CA)

(*) Notice: Subject to any disclaimer, the term of this patent is extended or adjusted under 35 U.S.C. 154(b) by 1361 days.

(21) Appl. No.: 11/342,522

(22) Filed: Jan. 31, 2006

(65) Prior Publication Data

US 2007/0177779 A1   Aug. 2, 2007

(51) Int. Cl.
G06K 9/00 (2006.01)
G06K 9/36 (2006.01)

(52) U.S. Cl. ..................... 382/132; 382/276

(58) Field of Classification Search ......... 382/128–132, 382/276, 155–158; 706/45–47; 345/660, 345/424, 426, 506, 419; 600/408, 300, 425; 703/5

See application file for complete search history.

(56) References Cited

U.S. PATENT DOCUMENTS

| | | | |
|---|---|---|---|
| 4,839,822 A | | 6/1989 | Dormond et al. |
| 5,058,176 A | | 10/1991 | Shimazaki et al. |
| 5,229,935 A | | 7/1993 | Yamagishi et al. |
| 5,261,050 A | | 11/1993 | Fox et al. |
| 5,447,153 A | | 9/1995 | Weil et al. |
| 5,542,003 A | * | 7/1996 | Wofford ............ 382/132 |
| 6,123,733 A | * | 9/2000 | Dalton ............ 703/5 |
| 6,219,059 B1 | | 4/2001 | Argiro |
| 6,268,870 B1 | | 7/2001 | Kato |
| 6,807,293 B2 | * | 10/2004 | Zavaljevski et al. ......... 382/128 |
| 6,987,872 B2 | * | 1/2006 | Dixon et al. ............ 382/128 |
| 7,062,714 B1 | | 6/2006 | Mo et al. |
| 7,310,095 B2 | * | 12/2007 | Matsumoto ............ 345/419 |
| 7,576,741 B2 | * | 8/2009 | Matsumoto ............ 345/424 |
| 7,778,451 B2 | * | 8/2010 | Matsumoto ............ 382/128 |

FOREIGN PATENT DOCUMENTS

JP   08180181   7/1996

(Continued)

OTHER PUBLICATIONS

Lai S H et al., "An adaptive window width/center adjustment system with online training capabilities for MR images" Artificial Intelligence in Medicine, Elsevier, NL LNKD - DOI: 10.1016/J. Artmed. 2004.03.008, vol. 33, No. 1, Jan. 1, 2005, pp. 89-101.

Couwenhoven M et al., "Enhancement method that provides direct and independent control of fundamental attributes of image quality for radiographic imagery" Proceedings of the International Society for Optical Engineering (SPIE), SPIE, USA LNKD - DOI: 10.1117/12.537272, vol. 5367, May 1, 2004, pp. 474-481.

(Continued)

Primary Examiner—Sherali Ishrat
(74) Attorney, Agent, or Firm—Bereskin & Parr LLP; Isis E. Caulder

(57) ABSTRACT

A system and method for determining a predicted window level transformation for image data associated with a loading image based on user selections of window level transformations. A learning image associated with a set of learning context characteristics is displayed to the user in order to elicit selection of a first selected window transformation. Learned rules are established based on the learning context characteristics and the first selected window transformation. When there is a request to display a loading image associated with a set of loading context characteristics, the learned rules are evaluated based on the loading context characteristics to determine a set of inferred window level transformations. The predicted window level transformation is then determined by selecting the most desirable inferred window level transformation.

23 Claims, 12 Drawing Sheets

FOREIGN PATENT DOCUMENTS

| | | |
|---|---|---|
| JP | 08278873 | 10/1996 |
| JP | 11235336 | 8/1999 |
| JP | 2002017685 | 1/2002 |
| JP | 2003102723 | 4/2003 |
| JP | 2004023408 | 1/2004 |
| JP | 2004049669 | 2/2004 |

OTHER PUBLICATIONS

European Search Report for Application No. EP 07 10 0313, dated Jul. 19, 2010.

* cited by examiner

CONFIGURATION CONTEXT RECORD

USER_ID = PETER
WORKSTATION_ID = PC005
SOURCE_STATION_ID = TYPE3
MODALITY_TYPE = CR
BODY_PART = HEAD
(COND) SLICE_POSITION = N/A

...

SEL_WINDOW_LEVEL_TRANSFORMATION = N/A

LEARNED CONTEXT RECORD

USER_ID = JOHN
WORKSTATION_ID = PC001
SOURCE_STATION_ID = TYPE1
MODALITY_TYPE = CR
BODY_PART = HEAD
(COND) SLICE_POSITION = N/A

...

SEL_WINDOW_LEVEL_TRANSFORMATION = [201230]

(COMPLETE) PREDICTED CONTEXT RECORD

USER_ID = JOHN
WORKSTATION_ID = PC001
SOURCE_STATION_ID = TYPE2
MODALITY_TYPE = CR
BODY_PART = HEAD
(COND) SLICE_POSITION = N/A

...

PRED_WINDOW_LEVEL_TRANSFORMATION = [234052]

FIG. 3B

CONFIGURATION RULES

CONFIG RULE034

IF: ...

CONFIG RULE035

IF: MODALITY_TYPE = "CR"
THEN: SLICE_POSITION = "N/A"

CONFIG RULE036

LEARNED RULES

LEARNED RULE024

IF: ...

LEARNED RULE025

IF: USER_ID = "JOHN"
AND
IF: BODY_PART = "HEAD"
AND
IF: MODALITY_TYPE = "CR"
AND
IF: SOURCE_STATION_ID = "TYPE 1"

THEN:
SEL_WINDOW_LEVEL_TRANSFORMATION = [201230]

LEARNED RULE026
IF: ...

FIG. 3D

WINDOW LEVELING SYSTEM AND METHOD

FIELD

The embodiments described herein relate to an image display system and method and more particularly to a system and method for performing window leveling for an image.

BACKGROUND

Commercially available image display systems in the medical field utilize various techniques to present medical images to a medical practitioner. Specifically, the images produced within modalities such as Computed Radiograph (CR), Magnetic Resonance Imagery (MRI) and the like are displayed on a display terminal for review by a medical practitioner at a medical treatment site. These medical images are displayed on a video monitor and the displayed images are used by the medical practitioner to determine the presence or absence of a disease, tissue damage etc.

Medical images, whether directly acquired from digital imaging modalities or from scanning films, are typically recorded with various intensities. Each dot (pixel) may be represented by a particular pixel intensity value. The acquired medical image may not always be satisfactory for radiologists' studies. For example, some medical images may be underexposed or overexposed. In order to improve readability the image brightness and/or contrast may need to be adjusted. Out of a number of various pixel intensity values, there is usually a certain range of pixel intensities values that is most useful for viewing any particular medical image or study.

The technique of window processing has been developed to improve the diagnosis of a region of interest in a diagnostic image. Because the tonal range of a region of interest may be small compared to the tonal range of the entire digital medical image, insufficient contrast in the region of interest may inhibit proper diagnosis. By expanding the tonal range in the region of interest to the entire tonal range of the display device through windowing, image contrast in the region of interest is greatly enhanced. Proper diagnosis is therefore greatly facilitated.

A particular pixel intensity value range of interest is defined as a "window". The distance between the two pixel intensity values at the two ends of the intensity range is called the "window width". As shown in FIG. 1, the "window width" is the range of pixel intensity values in the input digital medical image that are selected to be displayed over the full tonal range of the output display device. The intensity of "uninterested" pixels with values outside of the window are either mapped to black (i.e. fully underexposed) or white (i.e. fully overexposed). For example, in FIG. 1A, the window range is between 80 and 600. The pixel value of 100 is within the window, while the value of 40 is outside of the window and therefore would be mapped to "black". The pixel value of 700 is also outside of the window and would be mapped to "white".

The intensity of each medical image has a certain distribution. For example, tissues with higher density may produce a high number of "dark" pixels while less dense tissues will be more "bright" in the image. Unfortunately, the human eye is limited in its ability to discern intensities that are too similar. A "window level transformation" is a mathematical transformation that defines how to map pixel values within the window into display luminance values.

For example, if a medical practitioner wants to study a dense tissue area and wants to see as much detail as possible, it may be desired to select a level function like the one shown in FIG. 1. Even though pixel values 140 and 141 have a pixel intensity value difference of 1, after level function mapping, they will have a luminance difference of 5 when displayed. Human eyes will not be able to differentiate between two dots with pixel intensity values of 140 and 141 on a medical image film. However, the level function serves to stretch out the luminance displayed so that the two pixels with a luminance difference of 5 units can be easily differentiated within the leveled medical image.

Window and leveling parameters are most effective when they are tailored to different diagnostic tasks and to radiologist preferences. For example, a physician may want to focus on a specific area within a medical image such as the lung area in a chest x-ray. Typically, selection of window and level values is performed by an apparatus or method that enables a user to manually adjust window and level values within a particular area of interest. This manual method is however tedious and time consuming, especially when a user must select and readjust the window and level settings for each separate area of interest.

Also, in many instances, requirements for viewing medical imagery are time critical. Surgery may be necessary for immediate diagnosis and time is of the essence in such circumstances. It has been determined through medical practitioner usage studies that the main medical imagery workstation tool utilized is the window level transformation. The typical time to review a medical image study when window leveling is required has been determined to be approximately 100 seconds. In contrast, when no window leveling is required, the typical review time drops to 50 seconds.

Accordingly, a system that automatically, adaptively and transparently manipulates defined areas of a medical image and adjusts window and level values to display an image that requires little or no manual manipulation by a medical practitioner is highly desirable.

SUMMARY

The embodiments described herein provide in one aspect, a system for determining a predicted window level transformation for image data associated with a loading image, the system comprising:
 (a) a memory for storing a plurality of context characteristics and a set of learned rules that relate the context characteristics to at least one window level transformation;
 (b) a processor coupled to the memory for:
  (i) displaying a learning image associated with a set of learning context characteristics in order to elicit selection of a first selected window level transformation,
  (ii) establishing at least one learned rule based on the learning context characteristics and the first selected window level transformation, and storing the at least one learned rule within the memory;
  (iii) receiving a request to display the loading image, said loading image being associated with a set of loading context characteristics;
  (iv) evaluating the learned rules based on the loading context characteristics to determine a set of inferred window level transformations;
  (v) determining the predicted window level transformation by selecting the most desirable inferred window level transformation determined in (iv).

The embodiments described herein provide in another aspect a method for determining a predicted window level transformation for image data associated with a loading image, the method comprising:

(a) storing a plurality of context characteristics and a set of learned rules that relate the context characteristics to at least one window level transformation;

(b) displaying a learning image associated with a set of learning context characteristics in order to elicit selection of a first selected window level transformation;

(c) establishing at least one learned rule based on the learning context characteristics and the first selected window level transformation, and storing the at least one learned rule within the memory;

(d) receiving a request to display the loading image, said loading image being associated with a set of loading context characteristics;

(e) evaluating the learned rules based on the loading context characteristics to determine a set of inferred window level transformation; and (f) determining the predicted window level transformation by selecting the most desirable inferred window level transformation determined in (e).

Further aspects and advantages of the embodiments described herein will appear from the following description taken together with the accompanying drawings.

BRIEF DESCRIPTION OF THE DRAWINGS

For a better understanding of the embodiments described herein and to show more clearly how it may be carried into effect, reference will now be made, by way of example, to the accompanying drawings which show at least one exemplary embodiment, and in which:

FIG. 3B is a diagram illustrating the configuration context records, the learned context records and the prediction context records stored within the context records database of FIG. 2;

FIG. 3C is a diagram illustrating an excerpt from the configuration rules database of FIG. 2;

FIG. 3D is a diagram illustrating an excerpt from the learned rules database of FIG. 2;

Figure 1:
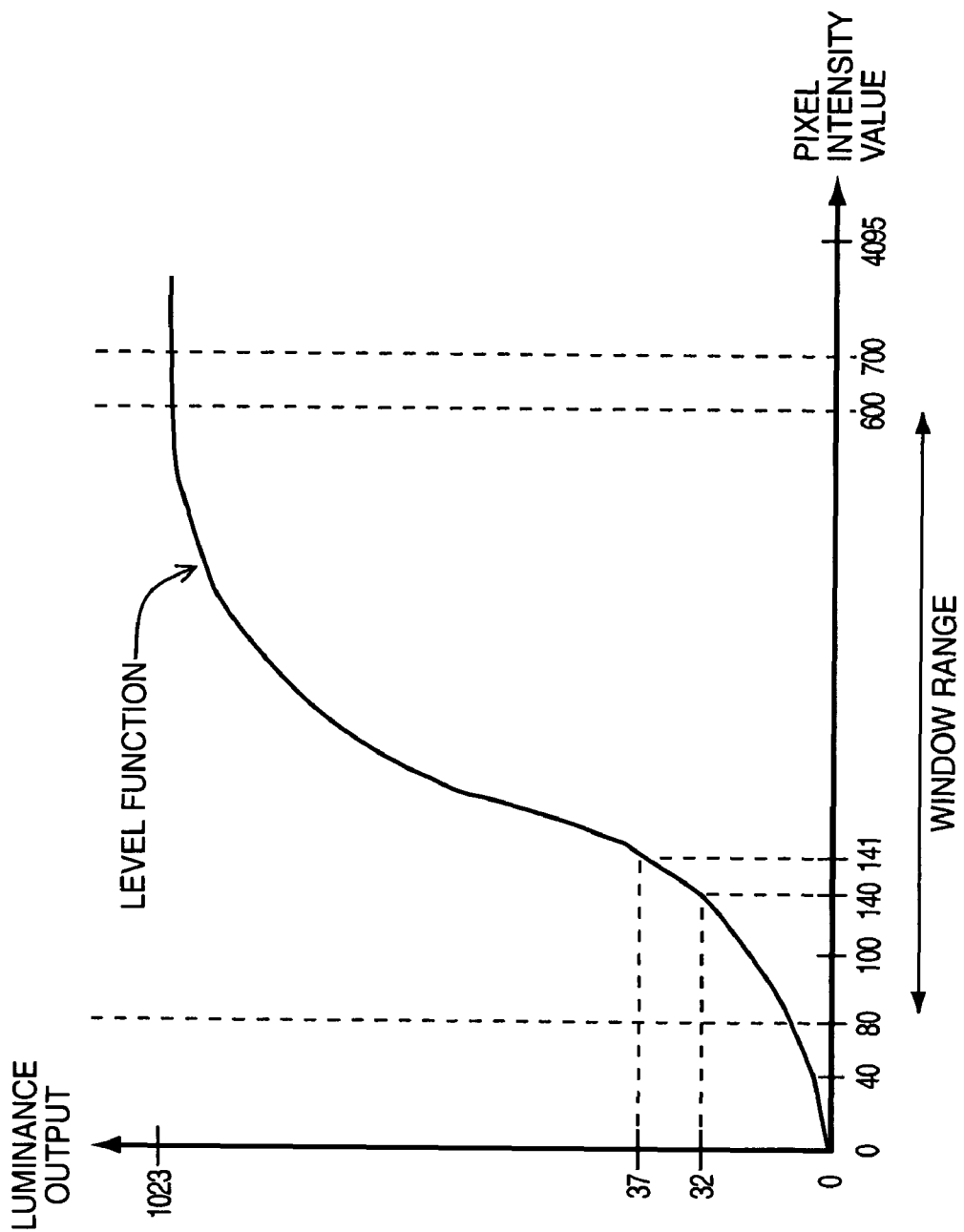
FIG. 1 is a graphical representation of a typical level function that defines the relationship between pixel intensity value and luminance output in order to illustrate the concepts of window leveling.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

Figure 2:
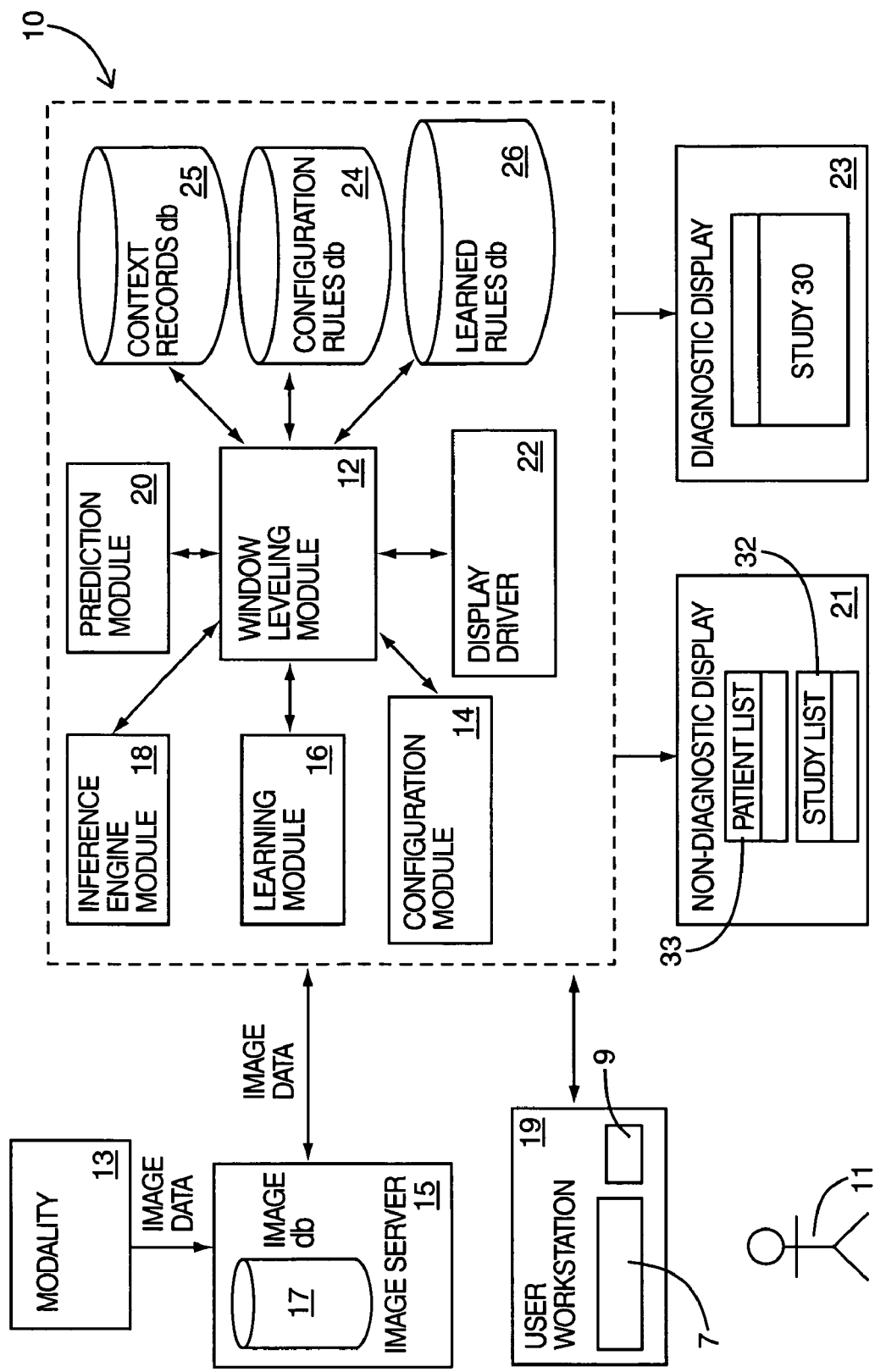
FIG. 2 is a block diagram of an exemplary embodiment of a window leveling system.

Reference is first made to FIG. 2, which illustrates the basic components of an exemplary embodiment of a window leveling system 10. Window leveling system 10 includes a window leveling module 12, a configuration module 14, a learning module 16, an inference engine module 18, a prediction module 20, a display driver 22, context records database 25, a configuration rules database 24, and a learned rules database 26. Medical image studies 30 (or any other type of image types such as series, or images) are generated by a modality 13 and stored in an image database 17 on an image server 15 where they can be retrieved by window leveling system 10. The window leveling system 10 determines a predicted window level transformation based on predetermined configuration rules, previous window level transformation selections and loading context characteristics associated with the image loading request. The window leveling system 10 then instructs the display driver 22 to apply the predicted window level transformation when displaying the study 30 on a diagnostic display 23.

The modality 13 is any conventional image data generating device (e.g. X-RAY equipment, Computed Tomography (CT) scanners, magnetic resonance (MR) images etc.) utilized to generate image data that corresponds to patient medical exams. A medical practitioner utilizes the image data generated by the modality 13 to make a medical diagnosis (e.g. for investigating the presence or absence of a diseased part or an injury or for ascertaining the characteristics of the diseased part or the injury). Modalities 13 may be positioned in a single location or facility, such as a medical facility, or may be remote from one another. The imaging modality 13 provides image data to the image server 15 in analog or any digital format used to represent medical image data (e.g. bitmaps, JPEGs, GIFs, etc.). The image server 15 then converts the image data into a digital format (i.e. an image data file) suitable for storage within the image database 17 on the image server 15.

The user workstation 19 includes a keyboard 7 and a user-pointing device 9 (e.g. mouse) as shown in FIG. 2. It should be understood that the user workstation 19 can be implemented by any wired or wireless personal computing device with input and display means (e.g. conventional personal computer, laptop computing device, personal digital assistant (PDA), etc.) User workstation 19 is operatively connected to the non-diagnostic display 21 and the diagnostic display 23. The image display system 10 is used to provide image display formatting depending on user inputs through the user workstation 19 and the user-pointing device 9. Image display system 10 is installed either on the hard drive of the user workstation 19 and/or on the image server 15 such that user workstation 19 works with the image server 15 in a client-server configuration.

The non-diagnostic display 21 is optimized for study 30 selection and provides a user 11 with a patient list 33 and a study list 32. Patient list 33 provides a textual format listing of patients for which studies 30 are available for display. Study list 32 provides a textual format listing of the display entities 27 (e.g. studies 30) that are available for display for the selected patient. The study list 32 also includes associated identifying indicia (e.g. body part, modality, etc.) and organizes the studies 30 in current and prior study categories. Typically, the user 11 will review study list 32 and select listed studies 30.

When the user 11 selects a study 30, the selected study 30 is displayed on the diagnostic display 23. Other associated textual information (e.g. patient information, image resolution quality, date of image capture, etc.) is simultaneously displayed within the study list 32 to assist the user 11 in selection of studies 30 for a particular patient. The non-diagnostic display 21 is preferably implemented using a conventional color computer monitor (e.g. a color monitor with a resolution of 1024×768). As discussed above, high-resolution graphics are not necessary for the non-diagnostic display 21 since this display is only displaying textual information to the user 11. In this discussion, it should be understood that the term "study" as used in the present disclosure covers all different images types (e.g. series, studies, images, etc.) without exclusion.

The diagnostic display 23 provides high resolution image display of studies 30. The diagnostic display 23 is preferably implemented using a medical imaging quality display monitor with a relatively high resolution typically used for viewing CT and MR studies (e.g. black and white "reading" monitors with a resolution of 1280-1024 and up).

The display driver 22 is a conventional display screen driver implemented using commercially available hardware and software. The display driver 22 ensures that the display entity 27 is displayed in a proper format on the diagnostic display 23. The display driver 22 is also able to dictate the particular window level transformation that is applied to the display entity 27 on diagnostic display 23 as will be further described. The non-diagnostic display 21 and diagnostic display 23 are preferably controlled and connected to the same processing platform. This processing platform must provide high speed processing and support at least two video cards (i.e. a regular video card for non-diagnostic display 21 and a high performance video graphics card for diagnostic display 23).

Figure 3A:
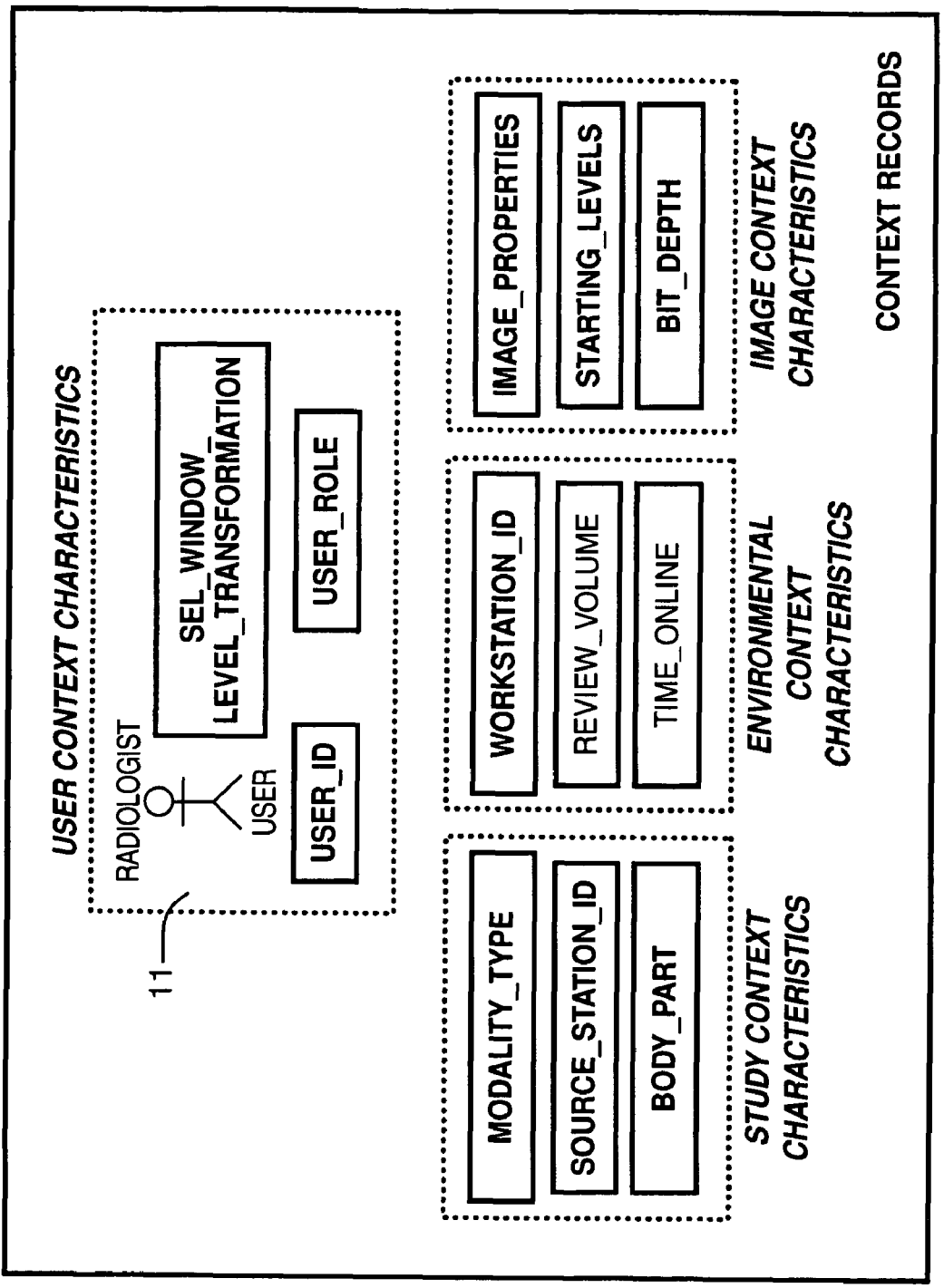
FIG. 3A is a block diagram of the various exemplary context characteristics within a user, study, environment and image contexts that can affect subjectively based window leveling preferences and which are modeled as primary and secondary context characteristics.

Now referring to FIGS. 2, 3A, 3B, 3C and 3D, the window leveling system 10 executes three general stages: a configuration stage, a learning stage and a prediction stage. The window leveling system 10 coordinates the operation of the configuration module 14, the learning module 16, the inference engine module 18 and the prediction module 20 in order to achieve "smart prediction" of a window level transformation based on observation and tracking of various context characteristics, some examples of which (e.g. user, study, environmental and image context characteristics) are illustrated in FIG. 3A.

In the configuration stage, the configuration module 14 gathers and stores configuration information associated with various context characteristics in one or more configuration context records (see FIG. 3B) within the context records database 25. The configuration module 14 then converts the configuration information into configuration rules (see FIG. 3C) for storage within the configuration rules database 24.

The configuration module 14 captures configuration information associated with context characteristics from various system data sources to populate and maintain up-to-date fields within the context record database 25. The configuration module 14 then applies analytical and machine learning tools, historical data, and heuristics to the configuration information stored within the context record database 25 to establish configuration rules within configuration rules database 24. These configuration rules reflect operational characteristics of various elements of the window leveling system 10 (e.g. modality types, source stations, client stations, system users, etc.).

For example, a configuration rule can be created that indicates that certain modalities have certain limitations in respect of the window level transformations that can be applied to the studies 30 generated by them. Further, certain relationships between various physical or non-physical system elements can be encoded within the configuration rules. In this way, configuration rules database 24 includes a set of configuration rules that define the basic operational and relationship characteristics of the elements of window leveling system 10.

In the learning stage, each time a user 11 loads a study the learning module 16 gathers and stores learned information associated with various associated learning context characteristics along with either a predicted or selected window leveling transformation in one or more learned context records (FIG. 3B) within context records database 25. The learning module 16 then converts this learned information into one or more learned rules (FIG. 3D) for storage in learned rules database 26. As will be further described the learning module 16 gathers and stores learned information as to whether or not the user the user performs window leveling (i.e. selects a different window level transformation).

The learning module 16 records a user's 11 selection of window level transformation (including the selection of the one already applied as a possibility) in response to the display of a study 30 on diagnostic display 23. Specifically, a study 30 is first displayed to the user 11 according to a particular (i.e. predicted) window level transformation (the derivation of the predicted window level transformation will be discussed later). The study 30 is also associated with a set of learning context characteristics. If the user 11 adjusts the window level transformation (i.e. according to subjective viewing preferences that have not been taken into account by the prediction), then the learning module 16 captures the learning context characteristics and the user selected window level transformation and updates relevant context records within context records database 25.

The learning module 16 analyzes the learned context records and translates the learned empirical relationships between the learned context characteristics into a learned rule for storing within the learned rules database 26. In this way, learned rules database 26 includes a set of learned rules that when combined together define the user's 11 preferences over time for various window level transformations based on the user's adjustment of window level settings over time.

In the prediction stage, the prediction module 20 determines a set of loading context characteristics associated with a user study request and directs the inference engine module 18 to determine a number of inferred window level transformation based on the loading context characteristics associated with a user's 11 image request as well as on relevant configuration rules (FIG. 3C) and learned rules (FIG. 3D). The prediction module 20 then determines the predicted window level transformation by selecting the most desirable inferred window leveling transformation. The prediction module 20 then stores it along with the loading context characteristics in a prediction context record and provides the predicted window level transformation to the window leveling module 12 for application to the study 30 through display driver 22 as will be described further.

The inference engine module 18 is provided with a set of loading context characteristics by the prediction module 20 and instructed to apply relevant configuration rules and learned rules to the loading context characteristics in order to arrive at a number of inferred window level transformations. As discussed above, the configuration rules database 24 includes a set of configuration rules that together define the operational and relationship characteristics of the elements of window leveling system 10. The learned rules database 26 includes a set of learned rules that when combined together define the user's 11 preferences over time for various window level transformations based on the user's adjustment of window level settings. The specific workings of the inference engine module 18 will be discussed further below.

Once the user 11 is provided with the requested study 30, as noted above the learning module 16 then monitors the user's 11 behaviour to determine whether the user 11 will select a different window level transformation than the predicted window level transformation. If so, then the loading characteristics along with the selected window leveling transformation is stored in the learned context record and the usual learning procedures regarding learned context characteristics etc. are conducted. However, if the user 11 does not select a different window leveling transformation, then the learning module 16 will convert the applicable predicted context record (including the predicted window leveling transformation) into a learned context record which will be transformed into a learned rule as will be discussed below.

Using this framework, the window leveling system 10 can, for example, adaptively learn over time if a given user workstation 19 is in a location that the user 11 believes requires a different window level transformation and if so pre-applies a predicted window level when studies 30 are retrieved in that location. Also, window leveling system 10 learns what kind of window leveling is applied for a particular image format or starting window level and then is able to pre-apply a predicted window level transformation when images of that format or starting window level are displayed. Finally, the system can also detect if the user is applying different window leveling based on time of day, length of active time online, or number of studies reviewed that day (i.e. objective context characteristics which may indicate user fatigue) and pre-apply a suitably predicted window level transformation as will be further discussed.

Referring specifically now to FIGS. 2 and 3A, the window leveling system 10 utilizes the fact that various subjective factors can affect the user's 11 preference for one window level transformation over another. The window leveling system 10 models these subjective factors as context characteristics (FIG. 3A) and monitors the user's 11 selection of window leveling functions over time to displayed studies 30. As shown in FIG. 3A, in one exemplary embodiment, the window leveling system 10 preferably differentiates between primary and secondary context characteristics when generating configuration and learned rules. Exemplary primary context characteristics are shown in bold format and the secondary context characteristics are shown in regular format in FIG. 3A.

Some example types of primary and secondary context characteristics are discussed below. However, it should be understood that different primary and secondary context characteristics could be utilized by the window leveling system 10. Also, it should be understood that different context characteristics may be considered primary or secondary by window leveling system 10.

User Context Characteristics

Various user related factors are modeled as user context characteristics and utilized within the determination of a predicted window level transformation for a particular study 30. For example, user related factors can include user identification (e.g. PETER, JOHN, JANE, etc.) (modeled as User_ID in FIG. 3A), user role (modeled as User_Role in FIG. 3A), the window level transformation selected by a user 11 (modeled as Sel_Window_Level_Transformation in FIG. 3A). The utility of the particular "role" of a user (e.g. a radiologist role or a neurosurgeons role) in a further embodiment of the window leveling system 10 will be discussed in respect of FIG. 9.

Study Context Characteristics

Various study related factors are also modeled as study context characteristics and used within the determination of a predicted window level transformation for a particular study 30. For example, information associated with the study 30 can include: modality type (modeled as Modality_Type in FIG. 3A), source station (modeled as Source_Station_ID in FIG. 3A), body part (modeled as Body_Part in FIG. 3A), etc.

Environmental Context Characteristics

Various environmental related factors are also modeled as environmental context characteristics and used within the determination of a predicted window level transformation for a particular study 30. Environmental context characteristics can include the user workstation 19 (modeled as Workstation_ID in FIG. 3A), the number of studies 30 a user 11 has reviewed in a session (modeled as Review_Volume in FIG. 3A), and the continuous active time a user 11 has spent online (modeled as Time_Online in FIG. 3A). By monitoring such objective data as the continuous active time a user has spent online or the number of studies reviewed by a user 11 within a session, it is possible for window leveling system 10 to recognize the needs of a user 11 as they experience increasing amounts of user fatigue and to make adjustments for such subjective factors by modeling these kinds of objective context characteristics.

Image Context Characteristics

Various factors relating to the image being displayed within a study 30 are also modeled as image context characteristics and used within the determination of a predicted window level transformation for the particular study 30. For example, information associated with the image being viewed within study 30 such as image properties (modeled as Image_Properties in FIG. 3A), starting levels (modeled as Starting_Level in FIG. 3A), and bit depth (modeled as Bit_Depth in FIG. 3A).

Referring again to FIGS. 2, 3A, 3B, 3C and 3D, values of these various context characteristics are determined during the configuration, learning and prediction stages of the operation of the window leveling system 10. Values of the context characteristics determined during the configuration stage are then stored as configuration context records within context records database 25. Values of the context characteristics determined during the learning stage are transferred from the prediction context record to the learned context record within context records database 25. The values of context characteristics (including the predicted window level transformation) determined during the prediction stage are stored as predicted context records within context records database 25. Configuration, learned and prediction context records are then available for retrieval by configuration module 14, learning module 16, prediction module 20 and inference engine module 18 as necessary for additional processing as will be described.

In the configuration stage, as discussed above, the configuration module 14 gathers and stores configuration information associated with various context characteristics in one or more configuration context records (FIG. 3B) within the context records database 25. The configuration module 14 then mines this configuration information and transforms the inherent relationships between the context characteristics into configuration rules (see FIG. 3C) for storage within the configuration rules database 24. Certain relationships between various physical or non-physical system elements are discovered and encoded within the configuration rules.

For example, if during the configuration stage, a user (e.g. User_ID="PETER") typically works at his user workstation 19 (e.g. Workstation_ID="PC005") and views a study 30 associated with a head body part image (e.g. Body_Part="HEAD") generated by a Computed Radiograph modality (e.g. Modality_Type="CR") using a TYPE 3 source station (e.g. Source_Station_ID="TYPE 3"), then the following context characteristic values will be associated with each other in a configuration context record within context records database 25: User_ID="PETER", Workstation_ID="PC005", Source_Station_ID="TYPE 3", Modality_Type="CR", and Body_Part="HEAD" as illustrated in FIG. 3B.

The configuration module 14 then mines this configuration information and transforms the inherent relationships between the learned characteristics into one or more learned rule(s) one of which is illustrated as "CONFIG RULE035" in FIG. 3C for storage within the configuration rules database 26. For example, it is known that a Computed Radiograph modality does not produce studies 30 having "slice positions". Accordingly, the configuration module 14 first determines and stores this kind of configuration information within configuration context record(s) and then this fact is used to transform this underlying inherent relationship between the Modality_Type and the Slice_Position context characteristic into a rule that reflects this fact (e.g. "CONFIG RULE035" in FIG. 3C) where if the Modality_Type="CR" then SLICE_POSITION="n/a" indicating that there can be no slice_positions within a study 30 generated by a CR-type modality. In this way, certain relationships between various context characteristics are discovered and encoded within the configuration rules.

In the learning stage, the learning module 16 monitors the user's 11 behaviour. When the user 11 performs window leveling, the learning module 16 determines and stores learned information associated with associated learned context characteristics in the predicted context record. Of particular interest is the user 11 selected window level transformation (i.e. "Sel_Window_Level_Transformation" in FIG. 3B) that is initially stored along with other relevant context characteristics in a predicted context record within context records database 25. Once the user 11 has either accepted or selected the predicted window leveling transformation, the predicted context record (including either the predicted or selected window level transformation) is transferred to a learned context record. The learning module 16 then mines this learned information and transforms the inherent relationships between the learned characteristics into learned rules for storage within the learned rules database 26. Certain relationships between various context characteristics are discovered and encoded within the learned rules.

For example, if during the learning stage, a user (e.g. User_ID="JOHN") at his user workstation 19 (e.g. Workstation_ID="PC001") selects a window level transformation (e.g. Sel_Window_Level_Function=[201230]) when viewing a study 30 associated with a head body part image (e.g. Body_Part="HEAD") generated by a Computed Radiograph modality (e.g. Modality_Type="CR") using a TYPE 1 source station (e.g. Source_Station_ID="TYPE 1"), then the following context characteristic values will (ultimately) be associated with each other in a learned context record within context records database 25: User_ID="JOHN", Workstation_ID="PC001", Source_Station_ID="TYPE 1", Modality_Type="CR", Body_Part="HEAD", and Sel_Window_Level_Transformation=[201230]. Again, it should be understood that this information is first stored in a predicted context record. The learning module 16 then mines this learned information and transforms the inherent relationships between the learned characteristics into a learned rule illustrated as "LEARNED RULE025" in FIG. 3D for storage within the learned rules database 26. In this way, certain relationships between various context characteristics are discovered and encoded within the learned rules.

In the prediction stage, as discussed above, the prediction module 20 monitors the user's 11 behaviour. When the user 11 requests the display of a study 30, the prediction module 20 determines a set of loading context characteristics that are associated with the user's 11 study request and stores them in a predicted context record (FIG. 3B) in the context record database which creates an "incomplete" prediction context record (i.e. with Pred_Window_Level_Transformation="n/a") that "awaits" the predicted window level transformation before it can be called "complete" (see FIG. 3B).

For example, if during the prediction stage, a user (e.g. User_ID=JOHN) views a study 30 at his workstation 19 (e.g. Workstation_ID="PC001") that is associated with a head body part image (e.g. Body_Part="HEAD") generated by a Computed Radiograph modality (e.g. Modality_Type="CR") using a TYPE 2 source station (e.g. Source_Station_ID="TYPE 2"), then the following loading characteristic values will be associated with each other in an "incomplete" predicted context record within context records database 25: User_ID="JOHN", Workstation_ID="PC001", Source_Station_ID="TYPE 2", Modality_Type="CR", "Body_Part="HEAD", and Sel_Window_Level_Function=[234052] as illustrated in FIG. 3B.

Then the prediction module 20 directs the inference engine module 18 to apply the relevant configuration rules (FIG. 3C) and learned rules (FIG. 3D) to the loading context characteristics (which are stored within the incomplete predicted record in FIG. 3B) to determine a predicted window level transformation. Inference engine module 18 applies the configuration rules and learned rules in order to determine the relative desirability of various inferred window level transformations associated with the configuration and learned rules as will be described further. The most desirable inferred window level transformation is then assumed to be the predicted window level transformation for the loaded image 30. The predicted window level transformation is then added into the predicted context record and the predicted context record is considered to be "complete".

After prediction, in the case where a user 11 has been presented with a displayed study 30 associated with a predicted window level transformation and the user 11 does not select a different window level transformation than the predicted window level transformation, then the learning module 16 will convert the applicable completed predicted context record into a learned context record (i.e. the predicted window leveling function was what the user 11 desired within a reasonable tolerance). This learned context record (previously a predicted context record) will be utilized to form a learned rule when the learning module 16 next updates the learning rules from the relationships stored within the learned context records.

Figure 4:
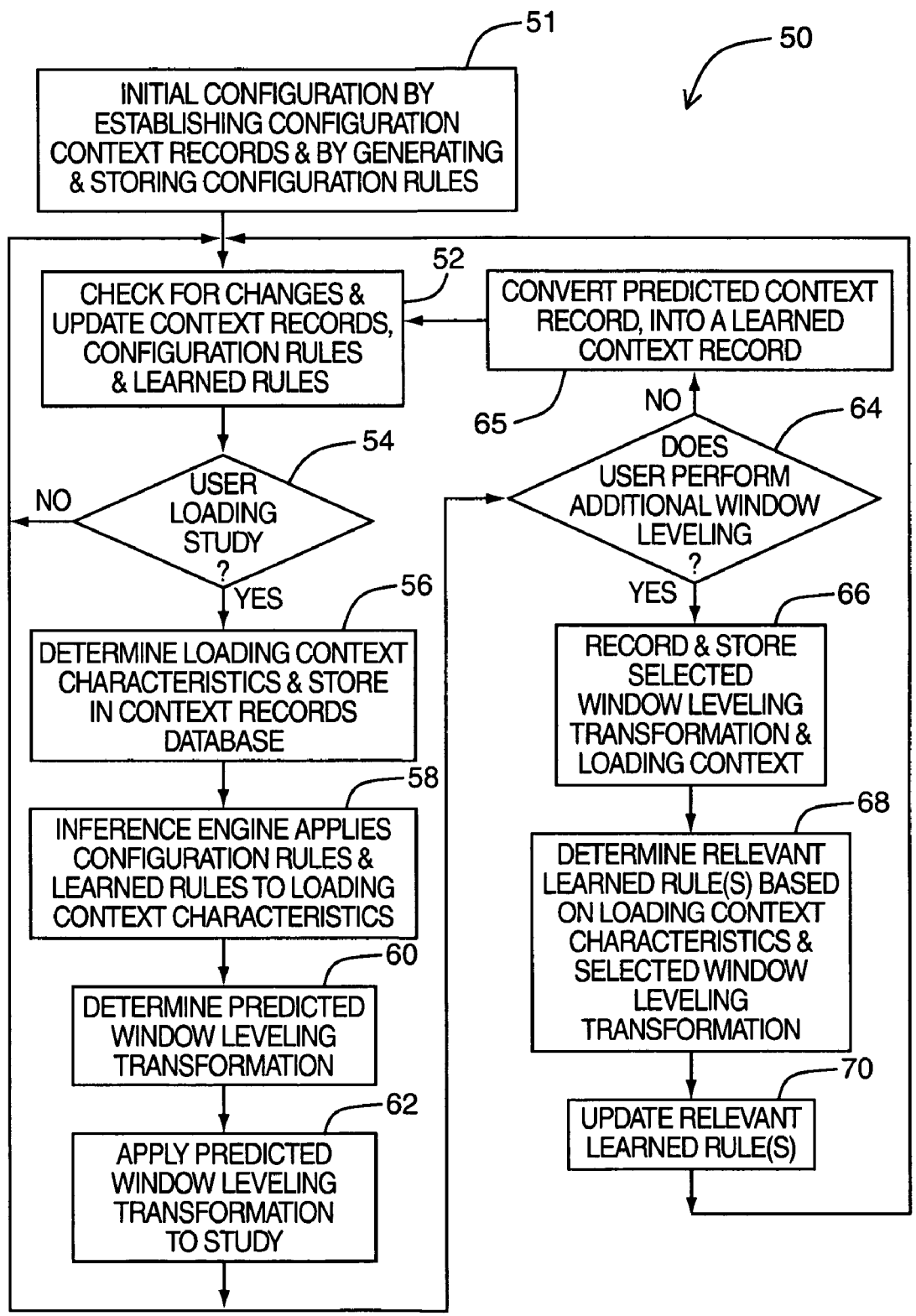
FIG. 4 is a flowchart illustrating the basic general operational steps of the window leveling system of FIG. 2.

Reference is now made to FIGS. 2, 3A, 3B, 3C, 3D, and 4. Specifically, FIG. 4 is a flowchart that illustrates the general operational steps 50 executed by the window leveling system 10.

At step (51), the window leveling module 12 instructs the configuration module 14 to perform an initial configuration. The configuration module 14 conducts an initial system configuration survey of each system element in order to establish an initial set of operational and relationship characteristics for each system element (e.g. for each system recorded system modality 13, image server 15, listed user 11, user workstation 19, diagnostic display 23, etc.) The configuration module 14 captures configuration information associated with context characteristics from various system data sources to populate and maintain up-to-date fields of configuration context records within the context record database 25. The configuration module 14 then applies analytical and machine learning tools, historical data, and heuristics to these configuration context records to establish default configuration rules and stores the configuration rules within configuration rules database 24. These configuration rules reflect operational characteristics of various elements of the window leveling system 10 (e.g. modality types, source stations, client stations, system users, etc.).

At step (52), the configuration module 14 checks for changes to the various operational and relationship characteristics of the elements of window leveling system 10. Changes to operational and relationship characteristics can include the addition or removal of recorded system modalities 13, image servers 15, listed users 11, user workstations 19, diagnostic displays 23, etc. into or from the window leveling system 10. For example, if a system user 11 accesses the window leveling system 10 from a new client station, a context characteristic Workstation_ID (i.e. an environment context characteristic), will be associated with the User_ID along with other relevant context characteristics in relevant configuration context records. The newly established configuration context records will then be translated by configuration module 14 into configuration rules. In this way, window leveling system 10 learns more about the user's 11 habits and their image viewing habits and maintains a current set of configuration rules that reflect these habits.

Also at step (52), the learning module 16 updates the learning rules based on analysis of the learned context records that uncovers the relationships stored within them. The learning module 16 analyzes the learned context records and translates the learned empirical relationships between the learned context characteristics into a learned rule for storing within the learned rules database 26. In determining learned rules, the learning module 12 considers the specific learned context characteristics present and compares them to the context characteristics associated with various other learned rules within user profile database. In this way, learned rules database 26 includes a set of learned rules that when combined together define the user's 11 preferences over time for various window level transformations based on the user's adjustment of window level settings over time.

At step (54), the window leveling module 12 determines whether user 11 is loading a new study 30 onto a user workstation 19. If not, then the window leveling module 12 goes back to step (52) to determine whether there have been any system configuration changes.

If the user 11 is loading a new study 30, then at step (56), the prediction module 20 determines the loading context characteristics associated with the user's 11 image request. As discussed above, loading context characteristics will include user (e.g. User_ID), study (e.g. Modality_Type, Source_Station, Body_Part), environmental (e.g. Workstation_ID, Review_Volume, Time_Online, etc.) and image (e.g. Image_Format, Starting_Levels) context characteristics that are associated with the user's loading request. The prediction module 20 then stores these loading context characteristics in an "incomplete" predicted context record within context records database 25.

At step (58), the prediction module 20 instructs the inference engine module 18 to apply the applicable configuration rules and learned rules to the loading context characteristics determined in step (56). Inference engine module 18 applies the configuration rules and learned rules in order to determine the relative desirability of various potential window level transformations associated with the configuration and learned rules as will be described further.

At step (60), the prediction module 20 selects the most desirable inferred window level transformation generated by inference engine module 18 to determine the predicted window level transformation. The prediction module 20 then provides window leveling module 12 with the predicted window level transformation.

Finally, at step (62), the window leveling module 12 applies the predicted window level transformation by instructing the display driver 22 to display the image on diagnostic display according to the predicted window level transformation.

At step (64), it is determined whether in spite of the image being displayed according to the predicted window level transformation, the user is performing additional window leveling.

If not, then back at step (65), the learning module 16 will convert the applicable predicted context record into a learned context record (i.e. the predicted window leveling function was what the user 11 desired within a reasonable tolerance) for transformation into a learned rule. That is, the next time the learning module 16 periodically updates the learning rules from the relationships stored within the learned context records this learned context record (previously a predicted context record) will be utilized to form a learned rule. As discussed above, context characteristics include user, study, environmental and image related characteristics that are present within the system at the time that the user 11 is performing window leveling adjustments.

At this point it should be understood that the phrase "loading context characteristics" will be used to represent the "learned context characteristics" previously discussed in this disclosure. While the learning and prediction stages are discussed separately, it should be understood that the learning and prediction stages typically are alongside each other. That is, while one study is loading and a predicted window level transformation is being determined for that one study, learning based on the user's 11 response to the displayed study 30 occurs.

If the user 11 is performing additional window leveling, then at step (66), the learning module 16 determines the learned context characteristics associated with the window leveling system 10 at the time that the user 11 is applying the window leveling. Accordingly, the learning module 16 will convert the predicted context record into a learned context record and replace the predicted window leveling transformation with the selected window leveling transformation.

At step (68), the learning module 16 determines one or more learned rules based on the learned context characteristics (i.e. the loaded context characteristics) determined in step

(56) and on the window level transformation selected by the user as determined in step (66). In determining learned rules, the learning module 12 considers the specific learned context characteristics present and compares them to the context characteristics associated with various other learned rules within user profile database. Specifically, the learning module 16 looks for instances of roughly similar context characteristics within context records database 25 as will be further explained.

At step (70), the learning module 16 updates the learned rules within learned rules database 26.

Figure 5:
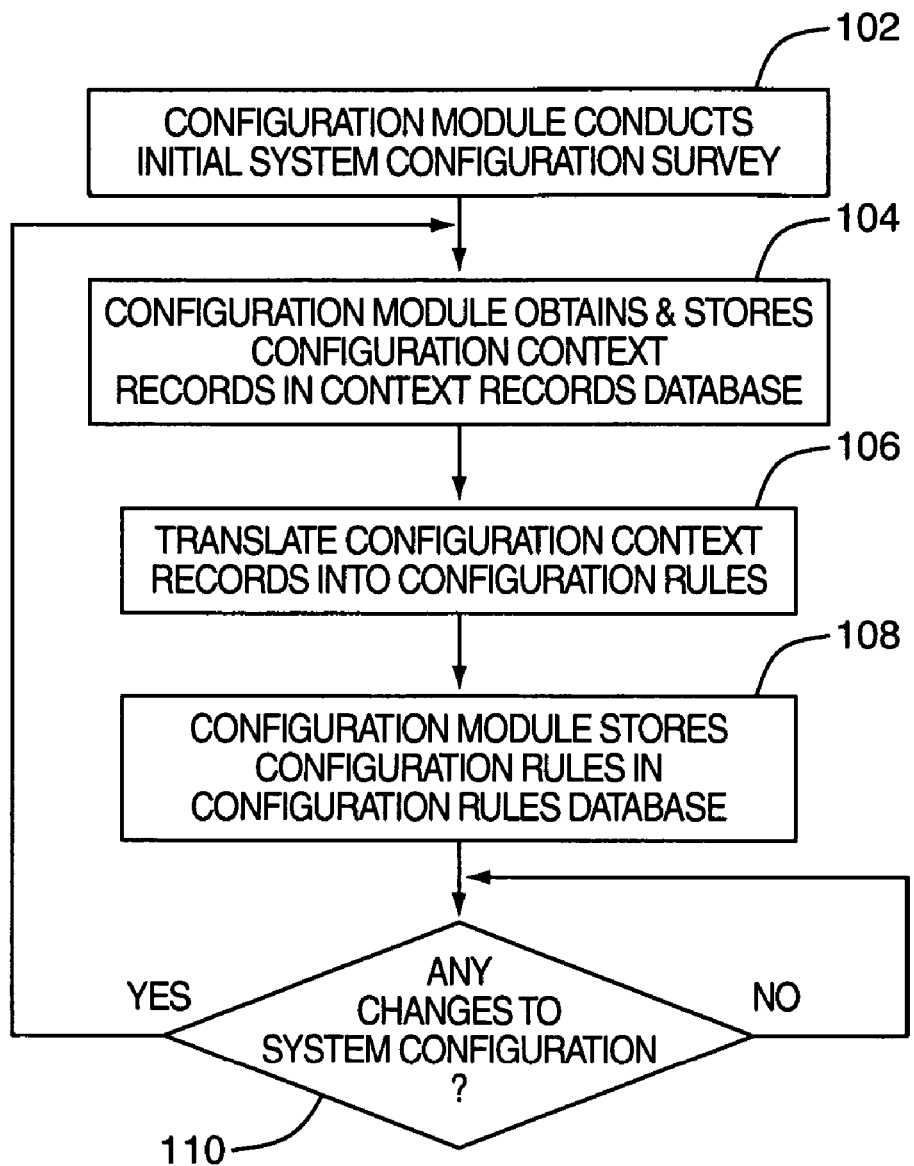
FIG. 5 is a flowchart illustrating the operational steps executed by the configuration module.

Reference is now made to FIGS. 2, 3A, 3B, 3C, 3D, and 5. Specifically, FIG. 5 is a flowchart that illustrates in more detail the operational steps 100 executed by the configuration module 14.

At step (102), the configuration module 14 conducts an initial system configuration survey of each element of window leveling system 10 in order to establish an initial set of operational and relationship characteristics for each system element (e.g. for each system recorded system modality 13, image server 15, listed user 11, user workstation 19, diagnostic display 23, etc.).

At step (104), the configuration module 14 captures configuration information associated with context characteristics from various system data sources to populate and maintain up-to-date fields of configuration context records within the context record database 25. Specifically, the configuration module 14 queries various system configuration tables and databases to obtain basic operational and relationship characteristics of the system elements. Once this information is obtained it is saved within configuration context records within the context records database 25.

At step (106), as discussed above, the configuration module 14 applies analytical and machine learning tools, historical data, and heuristics to the configuration context records to translate configuration context records into configuration rules.

At step (108), the configuration module 14 stores the configuration rules within the configuration rules database 24. These configuration rules reflect operational characteristics of various elements of the window leveling system 10 (e.g. modality types, source stations, client stations, system users, etc.).

At step (110), the configuration module 14 checks for changes to the various operational and relationship characteristics of the elements of window leveling system 10. Changes to operational and relationship characteristics can include the addition or removal of recorded system modalities 13, image servers 15, listed users 11, user workstations 19, diagnostic displays 23, etc. into or from the window leveling system 10.

If there are changes then again at step (104), the configuration module 14 establishes new configuration context records. Again, at step (106), the configuration module 14 then translates these new configuration context records into configuration rules. In this way, window leveling system 10 learns more about the user's 11 window level transformation preferences and their image viewing habits and maintains a current set of configuration rules that reflect these preferences.

Figure 6:
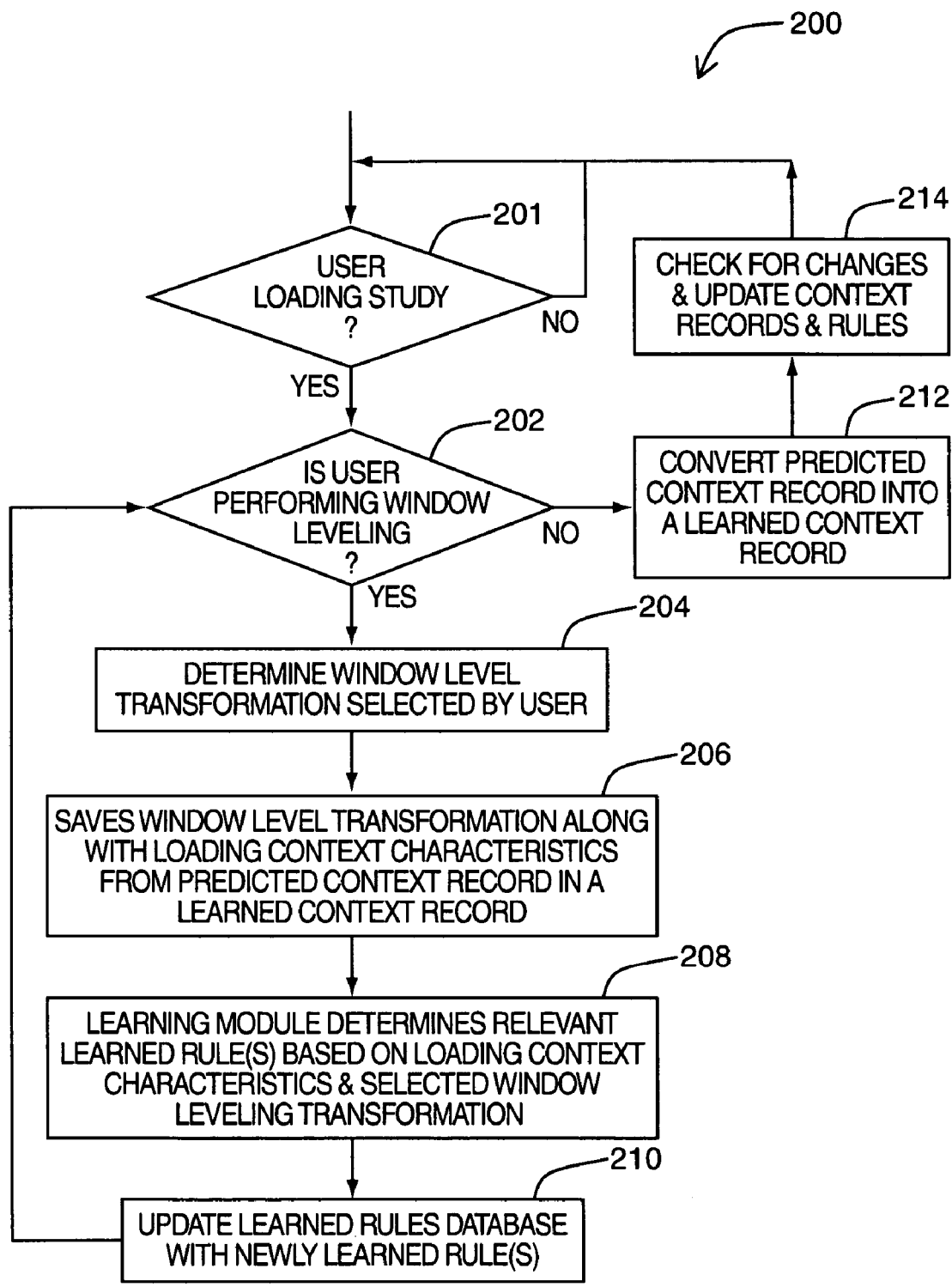
FIG. 6 is a flowchart illustrating the operational steps executed by the learning module.

Reference is now made to FIGS. 2, 3, and 6. Specifically, FIG. 6 is a flowchart that illustrates in more detail the operational steps 200 executed by the learning module 16.

At step (201), the learning module 16 determines whether the user 11 is requesting loading of a study 30. If not, then step (201) is repeated.

At step (202), the learning module 16 determines whether the user 11 is selecting a window level transformation (i.e. performing "window leveling") on a study 30. Again this is defined as where the user 11 selects a window level transformation that is different than the predicted window level transformation utilized to display the study 30. If not, then step (212) is executed as will be described below.

If so, then at step (204), the learning module 16 determines the different window level transformation selected by the user 11 and at step (206) stores it along with the loading context characteristics from the predicted context record as a learned context record within context records database 25.

At step (208), the learning module 16 translates the loaded context characteristics and the window level transformation stored within the learned context record into one or more learned rules. In determining learned rules, the learning module 12 considers the specific learned context characteristics present and compares them to the context characteristics associated with various other learned rules within learned rules database 24. Specifically, the learning module 16 looks for instances of roughly similar context characteristics within context records database 25 and conducts marginal analysis to determine one or more additional learned rules.

For example, consider a situation where a user 11 connects to window leveling system 10 from a different user workstation 19 and selects a particular window level transformation to view a similar image type from a similar modality type, etc. In such a situation, the learning module 16 determines display rule(s) that correlates the newly selected window level transformation with the new user workstation 19 as well as with various other loading context characteristics (e.g. time of day, modality type, source station, body part, etc.) One display rule that could be inferred is that the user 11 prefers a window level transformation with a wider window width when accessing the system from a different user workstation 19 than the user 11 normally prefers when accessing the system from the usual user workstation 19. This could be true in the case where the different user workstation 19 has a physical display with a larger width than the usual user workstation. In this way, as the user 11 applies a different pattern of window leveling to a similar image when they are at a different station, the window leveling system 10 will learn if a given station is in a location that the user 11 feels requires different window leveling to be applied.

At step (210), the learning module 16 updates the learned rules database 26 with the newly learned rule(s).

At step (212), the user 11 requested loading of a study 30 but then did not select a different window level transformation than the predicted window level transformation applied to the study 30. As a result at step (212), the learning module 16 converts the predicted context record into a learned context record. As noted above, when the user 11 requests a study 30 to be loaded, loading context characteristics are first stored in an "incomplete" predicted context record. Then predictor module 20 determines a predicted window level transformation and this is saved along with the loading context characteristic in a now "complete" predicted context record. If, after the study 30 is displayed to the user 11 with the applied predicted window level transformation and the user 11 does not apply any additional window leveling (i.e. does not select a distinct window level transformation), then the predicted context record is converted into a learned context record.

Finally at step (214), the learning module 16 checks for changes in the learned context records. The learning module 16 also analyzes the learned context records and translates the learned empirical relationships between the learned context characteristics into one or more learned rules for storing within the learned rules database 26. In determining learned rules, the learning module 12 considers the specific learned context characteristics present and compares them to the context characteristics associated with various other learned rules within user profile database as discussed in detail in respect of step (208).

In addition, the learning module 16 can be configured to determine learned rules according to an "aggression setting". That is, the learning module 16 could be configured to determine learned rules on a "highly aggressive" basis. In this case, the learning module 16 would determine learned rules with relatively few user selections of window leveling transformations where the values of at least one of the context characteristics (e.g. Modality_Type, Body_Part, and Sel_Window_Level_Transformation) associated with one window level transformation selection falls within a predefined tolerance range of the values of the same at least one context characteristic(s) associated with another window level transformation selection. While this approach could be undertaken by monitoring only a few context characteristics, more effective learning would result when monitoring the values of an appreciable number of context characteristics. While this approach may result in more variable learned rules at the beginning of a learning process, it would be more reactive and potentially suit user needs.

Alternatively, the learning module 16 could be configured to determine learned rules on a "less aggressive" basis. In this case, the learning module 16 would wait until a greater number of user selections of window leveling transformations where the value of at least one of the context characteristics (i.e. Modality_Type, Body_Part, and Sel_Window_Level_Transformation) associated with one window level transformation selection falls within a predefined tolerance range of the values of the same at least one of the context characteristics associated with another window level transformation selection. Again, while this approach could be undertaken by monitoring only a few context characteristics, more effective learning would result when monitoring the values of an appreciable number of context characteristics. While this approach may result in more variable learned rules at the beginning of a learning process, it would be more reactive and potentially suit user needs.

Figure 7:
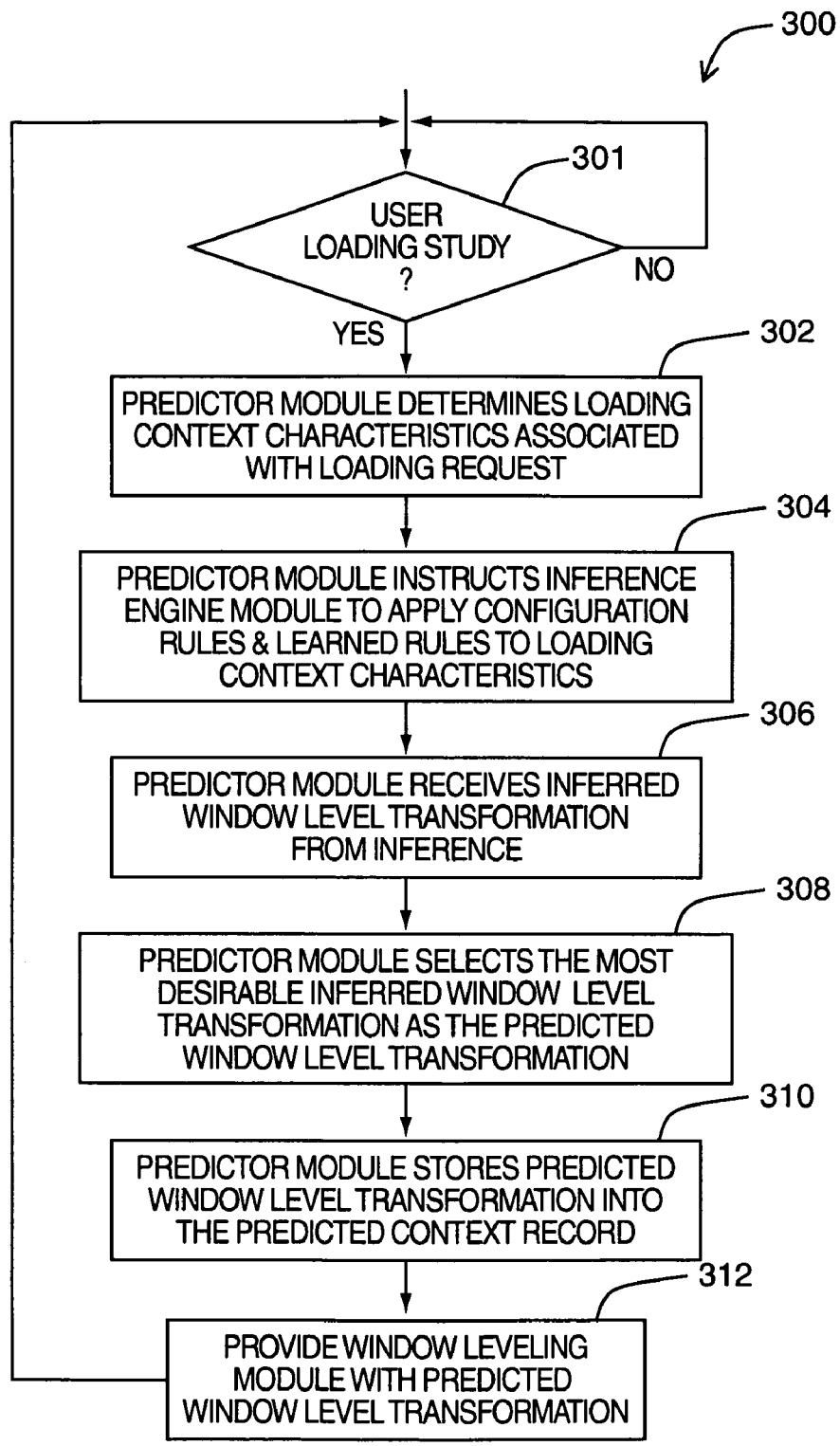
FIG. 7 is a flowchart illustrating the operational steps executed by the prediction module.

Reference is now made to FIGS. 2, 3, and 7. Specifically, FIG. 7 is a flowchart that illustrates the operational steps 300 executed by the prediction module 20.

At step (301), the learning module 16 determines whether the user 11 is requesting loading of a study 30. If not, then step (301) is repeated.

If the user 11 is requesting loading of a study 30, then at step (302), the prediction module 20 determines the loading context characteristics associated with the user's 11 image request. As discussed above, loading context characteristics will include user (e.g. User_ID), study (e.g. Modality_Type, Source_Station, Body_Part), environmental (e.g. Workstation_ID, User_Fatigue) and image (e.g. Image_Format, Starting_Levels) context characteristics that are associated with the user's loading request. The prediction module 20 then stores these loading context characteristics in an "incomplete" predicted context record (i.e. where Pred_Window_Level_Transformation=n/a") within context records database 25.

At step (304), the prediction module 20 instructs the inference engine module 18 to apply the applicable configuration rules and learned rules to the loading context characteristics determined in step (302). Inference engine module 18 applies the configuration rules and learned rules in order to determine the relative desirability of various potential window level transformations associated with the configuration and learned rules as will be described further.

At step (306), the prediction module 20 receives the various inferred window level functions from inference engine module 18.

At step (308), the prediction module 20 considers the inferred window level transformations generated by inference engine module 18 and selects the most desirable inferred window level transformation to determine the predicted window level transformation. It should be understood that this selection process can be implemented in various ways.

One example implementation is where the prediction module 20 determines the relative desirability of each inferred window level transformation by assigning a value to each inferred window level transformation. As will be explained, the inference engine module 18 utilizes certain learned rules to determine an inferred window function. Each learned rule is associated with certain context characteristics. The prediction module 20 assigns a value to a window level transformation based in part on how these certain context characteristics associated with the learned rules at issue, compare with the values of the loading context characteristics. For example, it could be calculated to what degree the respective context characteristics correspond to each other on a context characteristic by context characteristic basis. Another approach would be to calculate to what degree the context characteristic values associated with the learned rules differ from the loading context characteristics values on average (i.e. by considering an aggregation of context characteristics instead of by considering individual characteristics one by one).

In addition, in this exemplary implementation, it is preferred to distinguish between primary and secondary context characteristics within the loading context characteristics and within the context characteristics associated with the learned rules. Primary context characteristic values are preferably considered to be more heavily weighted than secondary context characteristic values. For example, consider a first inferred window level transformation that is associated with a learned rule that has a primary context characteristic value that is very close to the value of the corresponding loading context characteristic. Also consider a second inferred window level transformation is associated with a learned rule that has a secondary context characteristic value that is very close to the value of the corresponding loading context characteristic. The first inferred window level transformation will receive a heavier weighting benefit due to the closeness of the primary context characteristics than the second inferred window level transformation will from the closeness of its secondary context characteristic. It should be understood that this relationship could be utilized in an aggregated sense over all primary and secondary context characteristics associated with an inferred window level transformation being evaluated.

At step (310), the prediction module 20 stores the predicted window level transformation along with the loading context characteristics in a now "complete" predicted context record within context records database 25. If the learning module 16 later determines that the user did not conduct any additional window leveling, then the predicted context record will be considered a learned context record and one or more learned rules will be generated for future use.

Finally, at step (312), the prediction module 20 provides window leveling module 12 with the predicted window level transformation. The window leveling module 12 will then apply the predicted window level transformation by instructing the display driver 22 to display the image on diagnostic display according to the predicted window level transformation.

Figure 8:
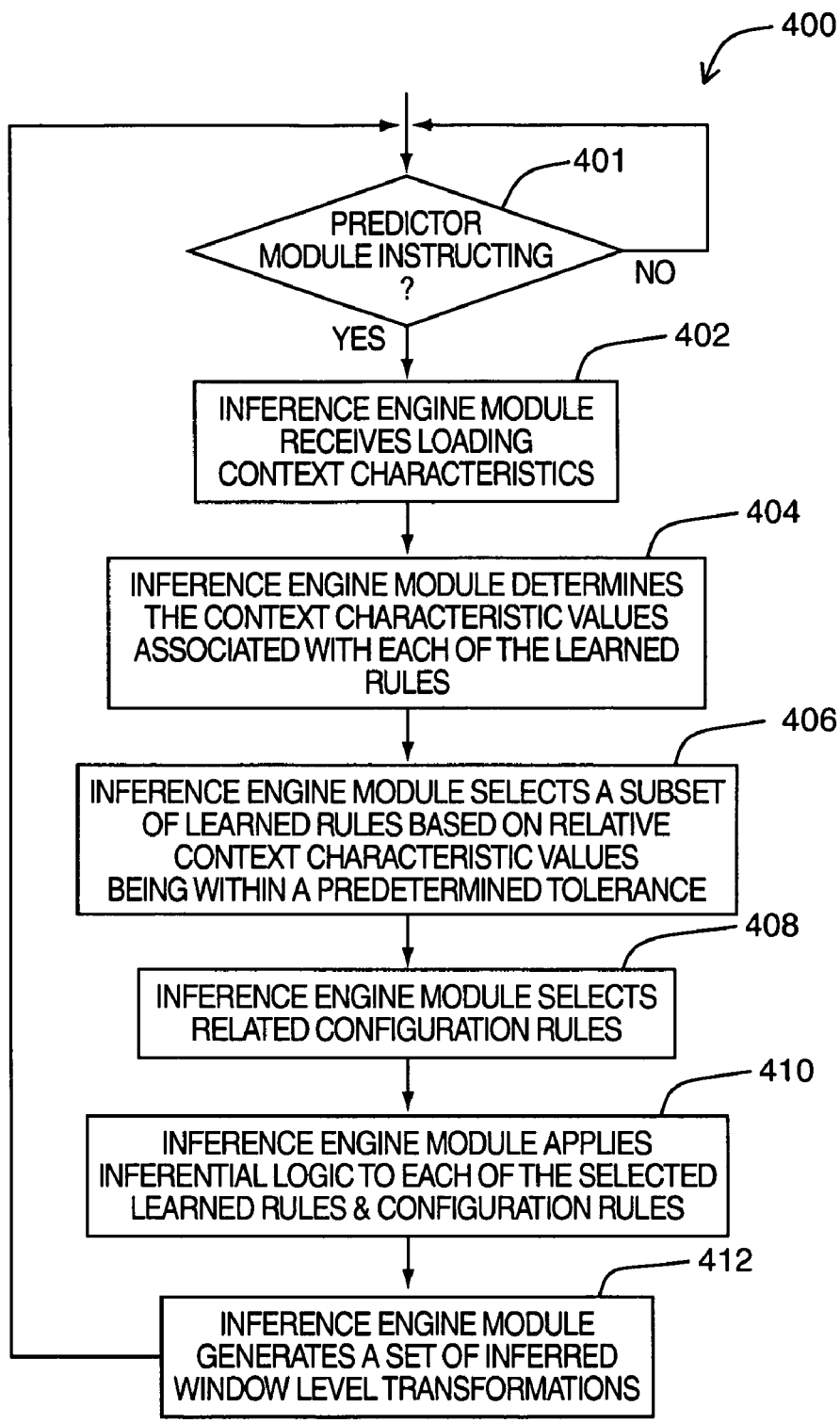
FIG. 8 is flowchart illustrating the operational steps executed by the inference engine module.

Reference is now made to FIGS. 2, 3A, 3B, 3C and 3D, and 8. Specifically, FIG. 8 is a flowchart that illustrates in more detail the operational steps 400 executed by inference engine module 18.

At step (401), the inference engine module 18 determines whether the prediction module 20 is instructing it to apply inference logic to the configuration rules and the learned rules in respect of a set of loading context characteristics.

At step (402), the inference engine module 18 obtains the set of loading context characteristics from the "incomplete" predicted context record within context records database 25 and accesses the configuration rules database 24 and the learned rules database 26.

The inference engine module 18 then applies inferential logic to the configuration rules, the learned rules, and the loading context characteristics to generate a set of inferred window level transformations. In general terms the inference engine module 18 first applies the configuration rules to the learned rules and then evaluates the learned rules based on the loading context characteristics to determine a set of inferred window level transformations. It should be understood that the operations required to conduct these steps could be implemented in various different ways. Also, it should be understood that inference engine module 18 could contain elements that could be implemented by various types of inference engine processing technology as will be discussed further.

As an exemplary implementation of these steps, at step (404), the inference engine module 18 determines the context characteristic values associated with each of the learned rules. That is, the inference engine module 18 reviews all of the learned rules within learned rules database 26 and for each learned rule determines the associated context characteristics and the values of those context characteristics. For example, referring back to FIG. 3D, the LEARNED RULE 25 contains the associated context characteristics "User_ID", "Body_Part", "Modality_Type" and "Source_Station" with values "JOHN", "HEAD", "CR" and "TYPE 1" respectively.

At step (406), the inference engine module 18 accesses the learned rule database 26 and selects a subset of these learned rules by selecting those learned rules that have at least one context characteristic value that corresponds to at least one corresponding loading context characteristics value according to a predetermined tolerance. That is, the inference engine module 18 only selects learned rules for further processing that have at least one context characteristic value that is within a predetermined "tolerance" (e.g. 5%) of a corresponding loading context characteristic value.

The concept of "tolerance" for this determination should be understood to mean some measure of "likeness" or "similarity". Essentially, the inference engine is only interested in considering learned rules that have some qualitative relevance to the loading context characteristics. One example way of defining "tolerance" would be determine whether the context characteristic values associated with the learned rules differ on average from the loading context characteristics values by less than a predetermined amount. One approach would be to analyze and plot recorded values to determine if they are statistically relevant, and if so, can be used as a learned value. It should be understood that there are many other approaches and quantitative requirements that could be used to implement the concept of "tolerance".

For example, referring back to FIG. 3B, the set of loading context characteristics as stored in the (complete) predicted context record indicates that the User_ID context characteristic has a value "JOHN", the Workstation_ID context characteristic has a value of "PC001", the Source_Station_ID context characteristic has a value of "TYPE2", the Modality_Type context characteristic has a value of "CR", the Body_Part context characteristic has a value of "HEAD". Accordingly, the inference engine module 18 selects learned rules that include context characteristics with values that are within a predetermined "tolerance" of the loading context characteristics as discussed above. For example, according to one predetermined tolerance since LEARNED RULE 025 (FIG. 3D) contains exact values "JOHN", "HEAD" and "CR" this learned rule could be considered even though it also contains the Source_Station_ID value "TYPE 1" (vs. the Source_Station_ID value "TYPE2").

At step (408), the inference engine module 18 then accesses the configuration rule database 24 and selects a subset of the configuration rules that relate to the context characteristics associated with the subset of the learned rules determined in step (406). For example, since LEARNED RULE 025 (FIG. 3D) was selected in step (406), various configuration rules that relate (i.e. have useful logical value) to the various context characteristic values of LEARNED RULE 25 will be selected. That is, since CONFIG RULE 035 (FIG. 3C) contains the context characteristic "Modality_Type" and since it has the value "CR", this configuration rule will be selected.

At step (410), the inference engine module 18 then applies inferential logic to each of the selected learned rules and each of the selected configuration rules to generate a set of inferred window level transformations at step (412). The inference engine module 18 can perform the required inference process using any of several methods. As discussed above, inference engine module 18 continuously adapts configuration and learned rules and conditions for application of those rules through adaptive and continuous learning methods, based on user 11 selections of window level transformations.

Inference engine module 18 could use weighting concepts to model "tolerance" as discussed above and to determine how to quantitatively apply certain configuration and learned rules. Weighting concepts such as artificial neural networks (ANNs), self-organizing maps (SOMs), decision trees, fuzzy rule-based systems, or model-based systems such as Hidden Markov Modeling (HMM) could be used either alone or in combination. Also, or alternatively, vector relationships could also be used to model "tolerance" as discussed above in order to assess and apply the configuration and learned rules (i.e. using concepts of "closest match" in vector space). Alternatively, the inference engine module 18 could be implemented, at least in part by Bayesian influence diagrams with inference procedures for operating on Bayesian networks as the inference procedures of the inference engine. Temporal reasoning procedures and value-of-information procedures could also be included within inference engine module 18.

Figure 9:
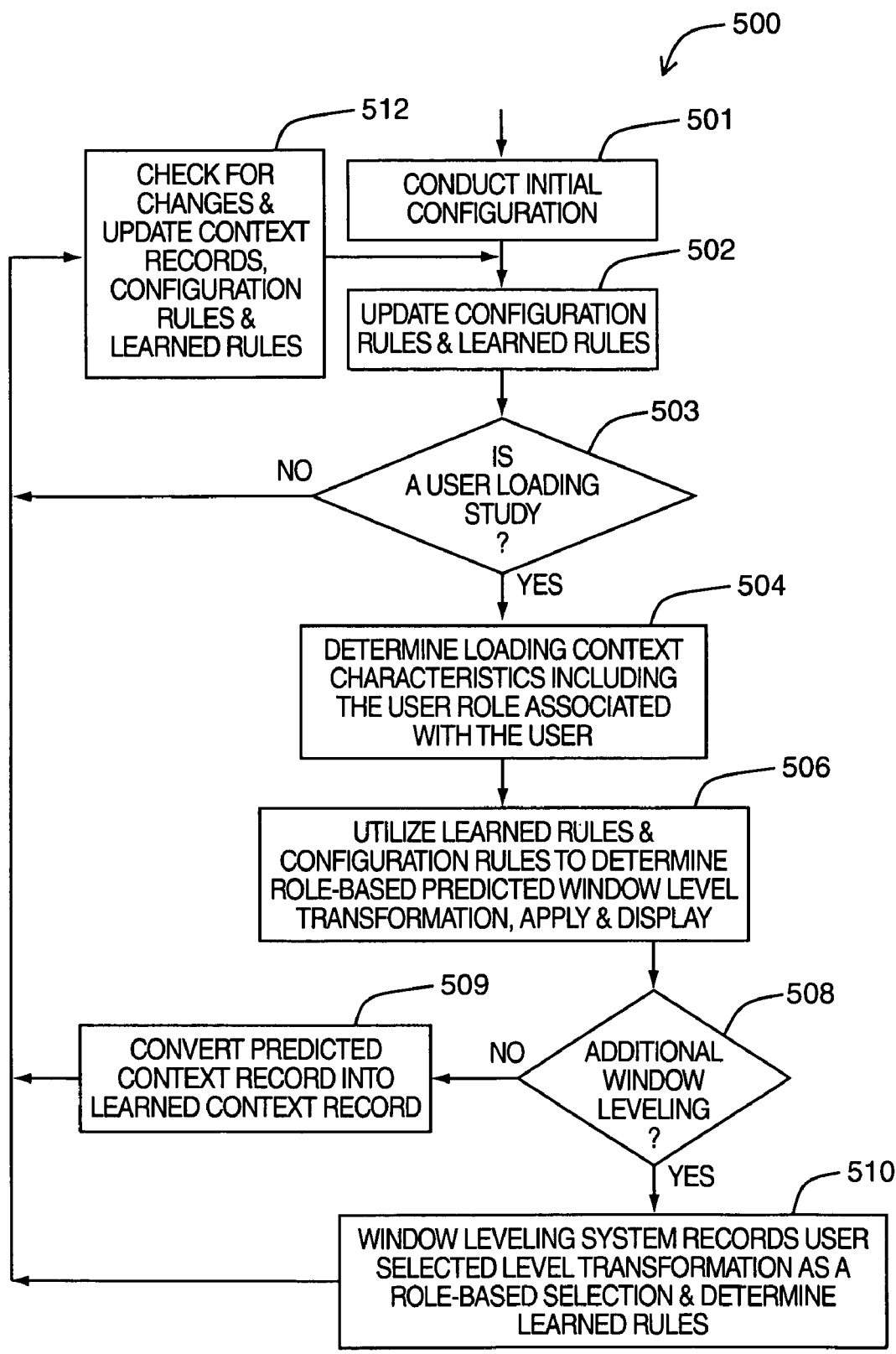
FIG. 9 is a flowchart illustrating another exemplary embodiment of the window leveling system of FIG. 2 that is based on user roles.

Now referring to FIGS. 2, 3A, 3B, 3C, 3D and 9, another exemplary embodiment is illustrated. Specifically, FIG. 9 is a flowchart that illustrates in more detail the operational steps 500 executed by window leveling system 10 when operating in a role-based capacity.

The window leveling system 10 was previously described as applying inference means to configuration rules and learned rules in respect of loading context characteristics. The window leveling system 10 was also described as establishing the learning rules that relate various learning context characteristics to at least one window level transformation. The loading and learning context characteristics utilized previously included user-related user or environmental related context characteristics such as "User_ID", "Workstation_ID" and "Review_Volume", and "Time_Online", and the like.

In contrast, the window leveling system 10 does not concern itself with such user-based related context characteristics and instead calibrates itself based on role-based context characteristics (e.g. "User_Role in FIG. 3A, namely radiologist, etc.). In this exemplary embodiment, the window leveling system 10 conducts role-based determinations of selections on a role by role basis, that is selections made by all users within a particular user "role" such as a radiologist or a neurosurgeon. The window leveling system 10 then calibrates itself based on these role-based determinations to provide a system-wide predicted window level transformation for application to all studies 30 being requested for display by all users 11 associated within that particular "role". That is, instead of factoring in the various user-related user or environmental related context characteristics (e.g. as discussed above "User_ID", "Workstation_ID" and "Review_Volume", and "Time_On-line", etc.), window leveling system 10 considers the user role (User_Role in FIG. 3A.

In this exemplary embodiment of the window leveling system 10, the configuration module 14, the learning module 16, the predictor module 20 and the inference engine module 18 are configured to disregard any user-related user or environmental related context characteristics. Also, the configuration rules database 24, the learned rule database 26 and the context records database 25 do not contain any user-related user or environmental related context characteristics. By removing user or environmental related context characteristics from the analysis, the window leveling system 10 is able to more efficiently provide a role-based predicted window level transformation for generally application across all user workstations 19 and all user roles.

At step (501), the window leveling system 10 conducts an initial configuration for the system by establishing context records and by generating and storing confirmation rules. This configuration stage has been discussed in detail above.

At step (502), the configuration rules and learned rules are updated within the configuration rules database 24 and the learned rules database 26.

At step (503), the window leveling system 10 determines whether a user 11 is loading a study 30. If not, then the window leveling system 10 re-executes step (501).

If the user 11 is loading a study 30 then at step (504), the window leveling system 10 determines the user role (i.e. User_Role of FIG. 3A) associated with user 11 (e.g. radiologist, neurosurgeon, etc.) along with other loading context characteristics. From here on, window leveling system 10 considers the particular user role instead of any user-related user or environmental related context characteristics within the subsequent learning and prediction stages.

At step (506), the window leveling system 10 utilizes predictor module 20 and inference engine module 18 to apply inference processing to the configuration rules and the learned rules to determine a role-based predicted window level transformation as discussed in relation to FIG. 4. This and the other steps in the method involve the use of the role-based context characteristic User_Role (FIG. 3A) instead of the previously discussed user-related user or environmental related context characteristics. The window leveling system 10 then applies the role-based predicted window level transformation to the study 30 at issue for display on the user workstation 19.

At step (508), it is determined whether a user 11 is selecting a different window level transformation than the role-based predicted window level transformation.

If so, then at step (510), the window leveling system 10 stores the user selected window level transformation along with the loading context characteristics within learned context record as a role-based selection. The window leveling system 10 then determines relevant learned rule(s) based on the loading characteristics and the selected window level transformation. In this way, users within a role are used to, over time, vary predicted window level transformations based on an overall (i.e. "democratic") role-based average.

If the user 11 is not selecting a different window level transformation, then at step (512), the window leveling system 10 converts the predicted context record into a learned context record and then step (512) is executed whereby changes are checked for and the context records, configuration rules and learned rules are updated.

It should be understood that various other modifications could be made to the operation of window level system 10 in order to change how the predicted window level transformation is obtained and how it is applies (e.g. independent of user, study, environment, and/or image context characteristics or any combination thereof).

Another exemplary embodiment of window leveling system 10 could include the above-noted role-based functionality described in respect of FIG. 9. along with the facility for measuring window leveling performed by users 11 and keeping track of various user utilization factors to weight certain user 11 feedback and its influence on the role-based predicted window level transformation. For example, users 11 that are more frequent users of the system or those that review a higher volume of studies 30 than other users 11. These kinds of user utilization factors could be used to identify certain users 11 as primary users within a role. Accordingly, window level transformations adopted by primary users within a role could then be recognized with heavier weight by learning module 18 and would accordingly have higher impact on the role-based predicted window level transformation. This kind of "representative" approach contrasts with the "democratic" approach described above but may provide a better "tuned" system that would satisfy frequent and/or high volume users 11.

Another exemplary embodiment of window leveling system 10 could include the use of the above-noted role-based functionality described in respect of FIG. 9 only to establish "default" or "baseline" settings for a new user 11. Specifically, when a new user 11 is added to the window leveling system 10, as discussed above, the user 11 would be assigned to a user role. The particular configuration and learned context records and rules which exist at the time that the new user 11 is added will be replicated for the new user 11 as their "own".

Subsequently, the user 11 will be allowed to "branch" from the role-based default or baseline settings depending on their particular selections of window leveling transformations. It should be understood that in this exemplary embodiment, in order to obtain the role-based results need to provide a particular user 11 with the default or baseline settings, the user context characteristic "User_Role" would be utilized to aggregate all configuration and learned context records and rules for each defined role. As discussed above in detail, the specific user-related user and environmental context characteristics would be utilized by the system in order to provide user-based determinations for the individual user 11 once certain initial settings have been provided.

Accordingly, the window leveling system 10 dynamically and adaptively applies a window level transformation to a user-selected study 30. The window level transformation, as discussed above, defines how to map pixel intensity values to display luminance's for a particular image. By monitoring how a user 11 manually performs window leveling in various viewing contexts, the system predicts a user's 11 desire for a particular window level transformation for a particular user selected study 30. By applying a predicted window level transformation to a user requested image, the need for the user 11 to perform additional window leveling is obviated in most cases and as a consequence, study review time is significantly reduced. The window leveling system 10 transparently manipulates defined areas of a study 30 and adjusts window and level values to display the study 30 in a manner that requires little or no manual manipulation by a user 11. Accordingly, the window leveling system 10 increases the speed at which medical diagnostic images can be made ready for delivery and diagnosis, as well as minimizes human intervention reducing unnecessary operator errors.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

GLOSSARY

Environment context characteristics—Environmental context characteristics consist of information associated with the environment in which the study is being viewed.

Image context characteristics—Image context characteristics consist of information associated with the image itself.

Predicted window level transformation—The predicted window level transformation represents a default window level transformation that is determined by the window leveling system and that is associated with a particular set of loading context characteristics.

Study context characteristics—Study context characteristics consist of information associated with a study itself.

User context characteristics—User context characteristics consist of information associated with a user.

Window level transformation—A window level transformation is a mathematical function that defines how to map pixel values within an image window into display luminances.

Window width—Window width is the range of pixel intensity values in the input digital image that is displayed over the full tonal range of the output display device.

The invention claimed is:

1. A system for determining a predicted window level transformation for image data associated with a loading image, the system comprising:
    (a) a memory for storing a plurality of context characteristics and a set of learned rules that relate the context characteristics to at least one window level transformation;
    (b) a processor coupled to the memory for:
        (i) displaying a learning image associated with a set of learning context characteristics in order to elicit selection of a first selected window level transformation,
        (ii) establishing at least one learned rule based on the learning context characteristics and the first selected window level transformation, and storing the at least one learned rule within the memory;
        (iii) receiving a request to display the loading image, said loading image being associated with a set of loading context characteristics;
        (iv) evaluating the learned rules based on the loading context characteristics to determine a set of inferred window level transformations;
        (v) determining the predicted window level transformation by selecting the most desirable inferred window level transformation determined in (iv).

2. The system of claim 1, wherein said system is also associated with a set of configuration context characteristics, and wherein the memory also stores the configuration context records and a set of configuration rules that relate configuration context characteristics to each other and wherein the processor evaluates the learned rules by applying the configuration rules to the learned rules and then evaluating the learned rules based on the loading context characteristics to determine a set of inferred window level transformations.

3. The system of claim 2, wherein the processor uses the configuration rules, the learned rules and the loading context characteristics to generate a set of inferred window level transformations by:
    (I) determining the context characteristic values associated with each of the learned rules;
    (II) selecting a subset of learned rules having at least one context characteristic value that corresponds to at least one corresponding loading context characteristics value according to a predetermined tolerance;
    (III) selecting a subset of the configuration rules that relate to the context characteristics associated with the subset of the learned rules determined in (II);
    (IV) applying inferential logic to each of the configuration rules selected in (III) and to the each of the learned rules selected in (II) to generate a set of inferred window level transformations.

4. The system of claim 3, wherein the selection of learned rules in (II) is made by determining whether the context characteristic values associated with the learned rules differ on average from the loading context characteristics values by less than a predetermined amount.

5. The system of claim 3, wherein the processor is adapted to further determine the relative desirability of each inferred window level transformation by assigning a value to each inferred window level transformation based on how the values of the loading context characteristics compare to the values of the associated learned context characteristics within the subset of learned rules determined in (II).

6. The system of claim 3, wherein the loading context characteristics include primary loading context characteristics and secondary loading context characteristics and wherein the processor assigns a value to each window level transformation according to a hierarchy wherein the values associated with the primary loading context characteristics are more heavily weighted than values associated with the secondary loading context characteristics.

7. The system of claim 1, wherein the processor is also used for:
    (vi) applying the predicted window level transformation to the loading image data; and
    (vii) displaying the result of the determination in (vi).

8. The system of claim 7, wherein the processor is also used for:
    (viii) determining if there is selection of a second selected window level transformation;
    (ix) if (viii) is false, then establishing at least one learned rule based on the loading context characteristics and the predicted window level transformation; and (x) if (vii) is true, then establishing at least one learned rule based on the loading context characteristics and the second selected window level transformation.

9. The system of claim 1, wherein each learned rule is established based on the learning context characteristics and the first selected window level transformation and an aggression level, wherein the aggression level represents the number of times that a window level transformation has been selected where the values of at least one context characteristic associated with one selected window level transformation fall within a predetermined tolerance range of the values of the same at least one context characteristic associated with another selected window level transformation.

10. The system of claim 1, wherein said loading and learning context characteristics are selected from the group consisting of: a user context characteristic, a study context characteristic, an environment context characteristic and an image context characteristic.

11. The system of claim 8, wherein at least one of:
A) the user context characteristic is selected from the group consisting of: a user identification, a user role, and the selected window level transformation;
B) the study context characteristic is selected from the group consisting of: a modality type, a source workstation identifier and a body part associated with the image data;
C) the environment context characteristic is selected from the group consisting of: a client workstation, volume of studies reviewed by a user, and time spent online by a user; and
D) the image context characteristic is selected from the group consisting of: image properties, starting window levels associated with the image data, and bit depth.

12. A method for determining a predicted window level transformation for image data associated with a loading image, the method comprising:
(a) storing a plurality of context characteristics and a set of learned rules that relate the context characteristics to at least one window level transformation;
(b) displaying a learning image associated with a set of learning context characteristics in order to elicit selection of a first selected window level transformation;
(c) establishing at least one learned rule based on the learning context characteristics and the first selected window level transformation, and storing the at least one learned rule within the memory;
(d) receiving a request to display the loading image, said loading image being associated with a set of loading context characteristics;
(e) evaluating the learned rules based on the loading context characteristics to determine a set of inferred window level transformation; and
(f) determining the predicted window level transformation by selecting the most desirable inferred window level transformation determined in (e).

13. The method of claim 12, further comprising storing a set of configuration context characteristics and a set of configuration rules that relate configuration context characteristics to each other and wherein the learned rules are evaluated by applying the configuration rules to the learned rules and then evaluating the learned rules based on the loading context characteristics to determine a set of inferred window level transformations.

14. The method of claim 12, wherein the configuration rules, the learned rules and the loading context characteristics are used to generate a set of inferred window level transformations by:
(I) determining the context characteristic values associated with each of the learned rules;
(II) selecting a subset of learned rules having at least one context characteristic value that corresponds to at least one corresponding loading context characteristics value according to a predetermined tolerance;
(III) selecting a subset of the configuration rules that relate to the context characteristics associated with the subset of the learned rules determined in (II);
(IV) applying inferential logic to each of the configuration rules selected in (III) and to the each of the learned rules selected in (II) to generate a set of inferred window level transformations.

15. The method of claim 14, wherein the selection of learned rules in (II) is made by determining whether the context characteristic values associated with the learned rules differ on average from the loading context characteristics values by less than a predetermined amount.

16. The method of claim 14, wherein the relative desirability of each inferred window level transformation is determined by assigning a value to each inferred window level transformation based on how the values of the loading context characteristics compare to the values of the associated learned context characteristics within the subset of learned rules determined in (II).

17. The method of claim 14, wherein the loading context characteristics include primary loading context characteristics and secondary loading context characteristics and wherein the processor assigns a value to each window level transformation according to a hierarchy wherein the values associated with the primary loading context characteristics are more heavily weighted than values associated with the secondary loading context characteristics.

18. The method of claim 12, further comprising:
(g) applying the predicted window level transformation to the loading image data; and
(h) displaying the result of the determination in (v).

19. The method of claim 18, further comprising:
(i) determining if there is selection of a second selected window level transformation;
(j) if (i) is false, then establishing at least one learned rule based on the loading context characteristics and the predicted window level transformation; and
(k) if (i) is true, then establishing at least one learned rule based on the loading context characteristics and the second selected window level transformation.

20. The method of claim 12, wherein each learned rule is established based on the learning context characteristics and the first selected window level transformation and an aggression level, wherein the aggression level represents the number of times that a window level transformation has been selected where the values of at least one context characteristic associated with one selected window level transformation fall within a predetermined tolerance range of the values of the same at least one context characteristic associated with another selected window level transformation.

21. The method of claim 12, wherein said loading and learning context characteristics are selected from the group consisting of: a user context characteristic, a study context characteristic, an environment context characteristic and an image context characteristic.

22. The method of claim 21, wherein at least one of
A) the user context characteristic is selected from the group consisting of: a user identification, a user role, and the selected window level transformation;
B) the study context characteristic is selected from the group consisting of: a modality type, a source workstation identifier and a body part associated with the image data;

C) the environment context characteristic is selected from the group consisting of: a client workstation, volume of studies reviewed by a user, and time spent online by a user; and D) the image context characteristic is selected from the group consisting of: image properties, starting window levels associated with the image data, and bit depth.

23. A non-transitory computer-readable medium upon which a plurality of instructions are stored, the instructions for performing the steps of the method as claimed in claim 12.

* * * * *